(12) United States Patent
Xiao et al.

(10) Patent No.: US 12,303,180 B2
(45) Date of Patent: May 20, 2025

(54) REFRIGERATION EQUIPMENT

(71) Applicant: PIEDMONT SCIENTIFIC (ZHUHAI) CO., LTD., Guangdong (CN)

(72) Inventors: Jiahua Xiao, Guangdong (CN); Dongbo Su, Guangdong (CN)

(73) Assignee: PIEDMONT SCIENTIFIC (ZHUHAI) CO., LTD., Guangdong (CN)

( * ) Notice: Subject to any disclaimer, the term of this patent is extended or adjusted under 35 U.S.C. 154(b) by 971 days.

(21) Appl. No.: 17/250,431

(22) PCT Filed: Jul. 17, 2019

(86) PCT No.: PCT/CN2019/096380
§ 371 (c)(1),
(2) Date: Jan. 20, 2021

(87) PCT Pub. No.: WO2020/020035
PCT Pub. Date: Jan. 30, 2020

(65) Prior Publication Data
US 2021/0282830 A1 Sep. 16, 2021

(30) Foreign Application Priority Data

Jul. 23, 2018 (CN) .......................... 201810812246.7
Oct. 18, 2018 (CN) .......................... 201811216757.9

(51) Int. Cl.
*F25B 41/40* (2021.01)
*A61B 18/02* (2006.01)
*A61B 18/00* (2006.01)

(52) U.S. Cl.
CPC .............. *A61B 18/02* (2013.01); *F25B 41/40* (2021.01); *A61B 2018/00023* (2013.01); *A61B 2018/00577* (2013.01)

(58) Field of Classification Search
CPC .......... A61B 18/02; A61B 2018/00023; A61B 2018/00577; A61B 2018/0212;
(Continued)

(56) References Cited

U.S. PATENT DOCUMENTS

| 5,275,595 | A | 1/1994 | Dobak, III |
| 6,442,949 | B1 | 9/2002 | Laskaris et al. |
| 2006/0122590 | A1* | 6/2006 | Bliweis ................. A61B 18/02 606/24 |
| 2008/0125764 | A1* | 5/2008 | Vancelette ............. A61B 18/02 606/22 |

(Continued)

FOREIGN PATENT DOCUMENTS

| CN | 103417288 A | 12/2013 |
| CN | 104873265 A | 9/2015 |

(Continued)

OTHER PUBLICATIONS

PCT/CN2019/096380 International Search Report English Translation, 2 pages dated Aug. 29, 2019.
(Continued)

*Primary Examiner* — Ankit D Tejani
*Assistant Examiner* — Joshua Brendon Solomon
(74) *Attorney, Agent, or Firm* — Boisbrun Hofman, PLLC (57) ABSTRACT

Provided is a refrigeration equipment comprising a storage tank, a delivery pipeline, a recovery pipeline, a cold energy generator, a first cold energy exchanger and a second cold energy exchanger. The refrigeration equipment can improve the utilization efficiency of cold energy, and can also advantageously control the rewarming process in an accurate way.

14 Claims, 2 Drawing Sheets

(58) Field of Classification Search
CPC ............. A61B 2018/0262; F25B 41/40; F25B 25/005; F25B 9/145
See application file for complete search history.

(56) References Cited

U.S. PATENT DOCUMENTS

| | | | |
|---|---|---|---|
| 2009/0124972 A1 | 5/2009 | Fischer et al. | |
| 2010/0256621 A1 | 10/2010 | Babkin et al. | |
| 2014/0039476 A1 | 2/2014 | Duong et al. | |
| 2014/0046312 A1 | 2/2014 | Ramadhyani et al. | |
| 2015/0018810 A1* | 1/2015 | Baust | F17C 9/00 62/50.7 |
| 2015/0297279 A1* | 10/2015 | Clarke | A61B 18/0218 606/22 |
| 2017/0000543 A1 | 1/2017 | Mahrouche et al. | |
| 2018/0310977 A1* | 11/2018 | Snyder | A61B 18/02 |

FOREIGN PATENT DOCUMENTS

| | | |
|---|---|---|
| CN | 106572877 A | 4/2017 |
| CN | 109009406 A | 12/2018 |
| CN | 109350220 A | 2/2019 |
| EP | 1080648 A2 | 9/2001 |
| EP | 1275914 A2 | 7/2002 |
| JP | 50-130859 | 10/1975 |
| JP | 62-294882 | 12/1987 |
| JP | 2003-125555 A | 4/2003 |
| JP | 2012522621 A | 9/2012 |
| WO | 2014025955 A2 | 2/2014 |
| WO | 2016025082 A1 | 2/2016 |
| WO | 2020020035 A1 | 1/2020 |

OTHER PUBLICATIONS

2018112167579 Chinese First Office Action dated Oct. 28, 2023 and English Translation, 16 pages.
2018112167579 Chinese Second Office Action dated Mar. 12, 2024 and English Translation, 20 pages.
2021-527269 Japanese Office Action dated Jan. 18, 2022 and English Translation, 18 pages.
19841708.1-1113 EP Office Action dated Jun. 22, 2021, 9 pages.

* cited by examiner

REFRIGERATION EQUIPMENT

CROSS-REFERENCE

This application is the National Stage of, and therefore claims the benefit of and priority to, International Application No. PCT/CN2019/096380, filed on Jul. 17, 2019, entitled "Refrigeration Equipment," and published as International Publication No. WO 2020/020035 A1 on Jan. 30, 2020, which claims the benefit of and priority to the Chinese patent application filed on Jul. 23, 2018, with the application number 201810812246.7, and to the Chinese patent application filed on Oct. 18, 2018, with the application number 201811216757.9. Each of the above applications are commonly assigned with this National Stage application, and the entireties thereof are hereby incorporated herein by reference.

TECHNICAL FIELD

The present application relates to the field of refrigeration technology, and particularly relates to a refrigeration equipment.

BACKGROUND

Refrigeration equipments are widely used in various fields, such as air conditioners, refrigerators, cold chain logistics, medical devices, etc., and usually comprises a cold energy generator such as a compressor, in cooperation with a cold carrier medium circulation system for delivering the cold energy to an object to be cooled. As the technology develops, many fields have raised higher requirements on parameters, of refrigeration equipments, such as cold energy utilization efficiency, quietness, volume, etc.

For example, in the field of medical devices, there is a kind of cryoablation apparatus, which usually comprises a cryoballoon and a main body providing a cold carrier medium to the cryoballoon, and in use, the cryoballoon is mounted on a front end of a catheter which extends into an exterior of a human body, the main body circulates the cold carrier medium through the catheter into the cryoballoon for cooling the cryoballoon, so as to cryo-ablate a target tissue.

Because cryoablation usually requires the cold head at a temperature of about −60° C., and in consideration of cold energy loss in the process, the temperature of the cold carrier medium has to reach at least −100° C. in order to smoothly carry out cryoablation, but it is very difficult for refrigeration equipments in prior art to reach this temperature. If an attempt is made by increasing the power of the cold energy generator, it would be restrained by the limited space in the operation room, and it would be difficult to meet the requirement of quiet environment in the operation room. Therefore, in the refrigeration equipments of prior art, because the efficiency of utilization of cold energy is low, it is difficult to meet the requirements of cold energy usage components such as a cryoballoon, and it is also difficult to reach the low temperature required by this kind of cold energy usage components.

SUMMARY OF THE INVENTION

Thus, a technical problem to be solved by the present application is how to overcome the defects that the refrigeration equipments in prior art has a low efficiency of utilization of cold energy and cannot reach the low temperature required by cold energy usage components, by providing a refrigeration equipment having a higher utilization efficiency of cold energy.

In order to solve the above technical problem, the present application provides the following technical solutions:

A refrigeration equipment, comprising:
a storage tank, for storing a cold carrier medium;
a delivery pipeline, having one end communicated with the storage tank and another end adapted for being communicated with a liquid inlet of a cold energy usage component;
a recovery pipeline, having one end communicated with the storage tank and another end adapted for being communicated with a liquid outlet of the cold energy usage component;
a first cold energy exchanger, mounted on the delivery pipeline and used for cooling the cold carrier medium flowing through the first cold energy exchanger by heat exchange;
a cold energy generator, for providing cold energy to the first cold energy exchanger;
and further comprising:
a second cold energy exchanger, having a hot fluid channel mounted on the delivery pipeline and a cold fluid channel mounted on the recovery pipeline, wherein, cold energy exchange occurs between the cold fluid channel and the hot fluid channel to precool the cold carrier medium flowing through the hot fluid channel, and the hot fluid channel is connected between the storage tank and the first cold energy exchanger.

Optionally, the refrigeration equipment further comprises:
a bypass pipe, communicated with the delivery pipeline and the recovery pipeline to allow the delivery pipeline and the recovery pipeline to form a precooling looping path connecting the storage tank and the first cold energy exchanger in series;
wherein the bypass pipe is communicated with the delivery pipeline via a first three-way valve.

Optionally, the refrigeration equipment further comprises:
a cold storage device, mounted on the recovery pipeline, communicated with the first cold energy exchanger via the bypass pipe, and adapted for storing cold energy coming from the first cold energy exchanger.

Optionally, the refrigeration equipment further comprises:
a heat-insulation device, having a heat-insulation chamber adapted for reducing or eliminating heat conduction to the exterior thereof, with the first cold energy exchanger, the second cold energy exchanger, the cold storage device and a cold energy output end of the cold energy generator located inside the heat-insulation chamber.

Optionally, the heat-insulation device is a box mounted with a vacuumizing device communicated with the heat-insulation chamber.

Optionally, the heat-insulation device is a box with the heat-insulation chamber thereof filled with heat insulation substance.

Optionally, the refrigeration equipment further comprises a rewarming looping path for transporting the cold carrier medium in the storage tank to the liquid inlet of the cold energy usage component.

Optionally, the rewarming looping path comprises:
a rewarming pipe;
wherein an inlet end of the rewarming pipe is connected by a second three-way valve to a side of the delivery pipeline that is located upstream of the first cold energy exchanger.

Optionally, the refrigeration equipment further comprises a rewarming looping path for transporting the cold carrier medium in the storage tank to the liquid inlet of the cold energy usage component after heating the cold carrier medium.

Optionally, the rewarming looping path comprises:
a rewarming pipe with a heating device connected in series;
wherein an inlet end of the rewarming pipe is connected by a second three-way valve to an upstream side of an inlet to the hot fluid channel.

Optionally, the rewarming looping path also comprises:
a rewarming backflow pipeline for connecting the liquid outlet of the cold energy usage component to a return port of the storage tank.

Optionally, the rewarming backflow pipeline comprises:
a rewarming backflow pipe having both ends thereof communicated with the recovery pipeline and being connected in parallel to the second cold energy exchanger;
wherein an inlet of the rewarming backflow pipe is connected by a third three-way valve to the delivery pipeline.

Optionally, the refrigeration equipment further comprises:
a heat-insulation device, having a heat-insulation chamber adapted for reducing or eliminating heat conduction to the exterior thereof, with the first cold energy exchanger, the second cold energy exchanger, a cold storage device and a cold energy output end of the cold energy generator located inside the heat-insulation chamber;
wherein the rewarming backflow pipe is located outside the heat-insulation device.

Optionally, a pumping device is connected in series on the delivery pipeline or the recovery pipeline, the pumping device is adapted for providing motive power for the flowing of the cold carrier medium.

The technical solutions of the present application have the following advantages:

1. The refrigeration equipment provided by the present application comprises a storage tank, a delivery pipeline, a recovery pipeline, a cold energy generator, a first cold energy exchanger and a second cold energy exchanger. The storage tank stores a cold carrier medium; the delivery pipeline has one end communicated with the storage tank and another end adapted for being communicated with a liquid inlet of a cold energy usage component; the recovery pipeline has one end communicated with the storage tank and another end adapted for being communicated with a liquid outlet of the cold energy usage component; the first cold energy exchanger is mounted on the delivery pipeline and used for cooling the cold carrier medium flowing through the first cold energy exchanger by heat exchange; the cold energy generator provides cold energy to the first cold energy exchanger; the second cold energy exchanger has a hot fluid channel mounted on the delivery pipeline and a cold fluid channel mounted on the recovery pipeline, wherein, cold energy exchange occurs between the cold fluid channel and the hot fluid channel to precool the cold carrier medium flowing through the hot fluid channel, and the hot fluid channel is connected between the storage tank and the first cold energy exchanger.

When using this refrigeration equipment to carry out refrigeration, the delivery pipeline, the recovery pipeline and the liquid inlet of the cold energy usage component are used to circulate the cold carrier medium to flow, and during the flow process, the cold energy generated at the cold energy generator is transferred to the delivery pipeline through the first cold energy exchanger and then transferred to the cold energy usage component, and the cold carrier medium flowing back to the recovery pipeline after cold energy is released still has a residual part of cold energy, then, when the cold carrier medium flows through the recovery pipeline, because of the existence of the second cold energy exchanger, the residual part of cold energy in the cold carrier medium in the recovery pipeline is transferred to the cold carrier medium in the delivery pipeline via the second cold energy exchanger, thereby causing the temperature of the cold carrier medium in the delivery pipeline to drop beforehand.

In the above process, because, on the delivery pipeline, the second cold energy exchanger is on an upstream side relative to the first cold energy exchanger where the cold carrier medium in the delivery pipeline has a temperature higher than that of the cold carrier medium in the recovery pipeline, it can therefore be ensured that cold energy is transferred from the recovery pipeline to the delivery pipeline. Through the above process, the residual cold energy of the cold carrier medium in the recovery pipeline can precool the cold carrier medium to reduce the initial temperature of the cold carrier medium entering the first cold energy exchanger, therefore, under the condition of the same cold energy exchange amount, such precooled cold carrier medium can reach a lower temperature, thereby improving the utilization efficiency of cold energy and meeting the requirements of low temperature for the cold energy usage component.

2. The refrigeration equipment provided by the present application further comprises a bypass pipe communicated with the delivery pipeline and the recovery pipeline to allow the delivery pipeline and the recovery pipeline to form a precooling looping path connecting the storage tank and the first cold energy exchanger in series, wherein the bypass pipe is communicated with the delivery pipeline via a first three-way valve. By using the bypass pipe, the cold carrier medium can be precooled before being circulated into the cold energy usage component, wherein, in a precooling step, the cold carrier medium comes out from the storage tank, sequentially flows through the delivery pipeline, the first cold energy exchanger, the bypass pipe and the recovery pipeline, and finally flows back into the storage tank. The precooled cold carrier medium has a reduced temperature to provide a lower initial temperature for the cold energy usage component, and thus the low temperature required by the cold energy usage component can be more easily reached after cooling again by the first cold energy exchanger. Therefore, this measure can further improve the efficiency of utilization of cold energy of the refrigeration equipment.

3. The refrigeration equipment provided by the present application further comprises a cold storage device which is mounted on the recovery pipeline, communicated with the first cold energy exchanger via the bypass pipe, and adapted for storing cold energy coming from the first cold energy exchanger. In the precooling step, the cold storage device can store a part of cold energy brought by the cold carrier medium, and later, this part of stored cold energy can precool the cold carrier medium flowing out of the cold energy usage component, so as to increase the temperature difference between the cold fluid channel and the hot fluid channel at the second cold energy exchanger, increase the cold energy exchange rate at the second cold energy exchanger, and thus further reduce the temperature of the cold carrier medium in the delivery pipeline, and this precooled cold carrier medium can reach a lower temperature after finally being cooled by the first cold energy exchanger. Therefore, this measure can further reduce the lowest temperature that can be reached by the refrigeration equipment, and can further improve the efficiency of utilization of cold energy and reduce waste of cold energy.

4. The refrigeration equipment provided by the present application further comprises a heat-insulation device which has a heat-insulation chamber adapted for reducing or eliminating heat conduction to the exterior thereof, with the first cold energy exchanger, the second cold energy exchanger, the cold storage device and a cold energy output end of the cold energy generator located inside the heat-insulation chamber. By using the heat-insulation device, loss of cold energy can be prevented during the cold energy exchanging process, and meanwhile the heat preservation effect of the cold storage device is better, as loss of cold energy from the cold storage device is prevented during the cold energy storing process.

5. In the refrigeration equipment provided by the present application, the heat-insulation device is a box mounted with a vacuumizing device communicated with the heat-insulation chamber. The heat-insulation chamber in a near-vacuum state can further reduce the loss rate of cold energy, and thus help the refrigeration equipment further improve the efficiency of utilization of cold energy.

6. The refrigeration equipment provided by the present application further comprises a rewarming looping path for transporting the cold carrier medium in the storage tank to the liquid inlet of the cold energy usage component after heating the cold carrier medium. In some scenarios, the cold energy usage component needs to raise its temperature, for example, in a cryoablation operation, the refrigerated target tissue needs to be rewarmed. The rewarming looping path provided in the present application can heat the cold carrier medium and transport the cold carrier medium to the target tissue through a catheter, such a separately arranged rewarming looping path not only can meet the demands of rewarming of the cold energy usage component, but also is very beneficial for accurately controlling the temperature, procedure and time of the rewarming, thereby increasing surgical cure rate and reducing postoperative complications.

7. In the refrigeration equipment provided by the present application, the rewarming looping path comprises a rewarming pipe with a heating device connected in series, wherein an inlet end of the rewarming pipe is connected by a second three-way valve to an upstream side of an inlet to the hot fluid channel. By connecting the rewarming pipe to the upstream side of the second cold energy exchanger on the delivery pipeline, the rewarming pipe is connected in parallel to the first cold energy exchanger and the second cold energy exchanger, so that the pipeline for heating the cold carrier medium is independent from the pipeline for cooling the cold carrier medium. Therefore, interference to the heating process of the cold carrier medium caused by residual cold energy of the first cold energy exchanger and the second cold energy exchanger can be prevented in the rewarming step, thereby reducing interference factors in the rewarming process, and making it easier to control the rewarming process.

8. In the refrigeration equipment provided by the present application, the rewarming looping path comprises a rewarming backflow pipeline for connecting the liquid outlet of the cold energy usage component to a return port of the storage tank. The separately arranged rewarming backflow pipeline can make the rewarming process form an independent rewarming loop composed of the storage tank, the rewarming pipe, the cold energy usage component, and the rewarming backflow pipeline, thereby further reducing interference factors in the rewarming process, and making the control of the rewarming process more accurate.

9. The refrigeration equipment provided by the present application further comprises a heat-insulation device which has a heat-insulation chamber adapted for reducing or eliminating heat conduction to the exterior thereof, with the first cold energy exchanger, the second cold energy exchanger, a cold storage device and a cold energy output end of the cold energy generator located inside the heat-insulation chamber, wherein the rewarming backflow pipe is located outside the heat-insulation device. As the rewarming backflow pipe is arranged outside the heat-insulation device, it can be prevented that the cold energy in the cold storage device or the second cold energy exchanger is brought away by the rewarming backflow pipe when transporting the cold carrier medium after rewarming, so as to improve the utilization rate of cold energy.

In conclusion, the refrigeration equipment provided by the present application can improve the efficiency of utilization of cold energy, and can also advantageously control the rewarming process in an accurate way.

BRIEF DESCRIPTION OF THE DRAWINGS

In order to describe the technical solutions more clearly in the specific embodiments of the present application or in the prior art, hereinafter, the appended drawings used for describing the specific embodiments or the prior art will be briefly introduced. Apparently, the drawings described below show only some embodiments of the present application, and for a person skilled in the art, without expenditure of creative labor, other drawings can be derived on the basis of these appended drawings.

REFERENCE SIGNS

1—storage tank, 2—delivery pipeline, 3—recovery pipeline, 4—cold energy generator, 5—first cold energy exchanger, 6—second cold energy exchanger, 7—catheter, 8—cold head, 9—bypass pipe, 10—first three-way valve, 11—cold storage device, 12—heat-insulation device, 13—heat-insulation chamber, 14—vacuumizing device, 15—rewarming pipe, 16—heating device, 17—second three-way valve, 18—rewarming backflow pipe, 19—third three-way valve, 20—pumping device, 21—flowmeter, 22—thermometer, 23—one-way valve, 24—heat radiator.

DETAILED DESCRIPTION OF EMBODIMENTS

A clear and complete description of the technical solutions of the present application is given below, in conjunction with the appended drawings. Apparently, the described embodiments are a part, but not all, of the embodiments of the present application. All the other embodiments, derived by a person skilled in the art on the basis of the embodiments described in the present application without expenditure of creative labor, are included in the protection scope of the present application.

In the description of the present application, it needs to be noted that, terms such as "center", "above", "below", "left", "right", "vertical", "horizontal", "inside", "outside" refer to the orientation or positional relation based on the illustration of the drawings, which is merely for facilitating and simplifying the description of the present application, not for indicating or implying that the referred apparatus or component must have a particular orientation or must be configured or operated in a particular orientation, therefore is not to be construed as a limitation towards the present application. In addition, terms such as "first", "second", "third" are merely for the purpose of description, and are not to be construed as an indication or implication of relative importance thereof.

In the description of the present application, it needs to be noted that, unless specifically defined or restricted otherwise, terms such as "mount", "interconnect", "connect" should be broadly construed, for example, they may be fixed connection or detachable connection or integral connection; they may be mechanical connection or electrical connection; they may be direct connection, or indirect connection via an intermediate medium, or internal communication between two units. For a person skilled in the art, the specific meaning of the afore-mentioned terms in the present application can be understood according to specific situations thereof.

Furthermore, the technical features involved in different embodiments of the present application described below can be combined with one another as long as they do not conflict with one another.

Embodiment 1

FIG. 1 to FIG. 4 show Embodiment 1 of the present application, the present embodiment provides a refrigeration equipment which may be used for refrigerating a cold head 8 in a cryoablation apparatus, but is not limited to being applied in a cryoablation operation, the refrigeration equipment provided by the present application may also be used in other apparatuses having a cold energy usage component for carrying out precooling, refrigerating and rewarming, for example, in refrigerators, air conditioners, cold chain logistic trucks, etc. And for clarity of description, in the present embodiment, a situation where the cold energy usage component is a cold head 8 of a cryoablation apparatus is introduced.

Figure 1:
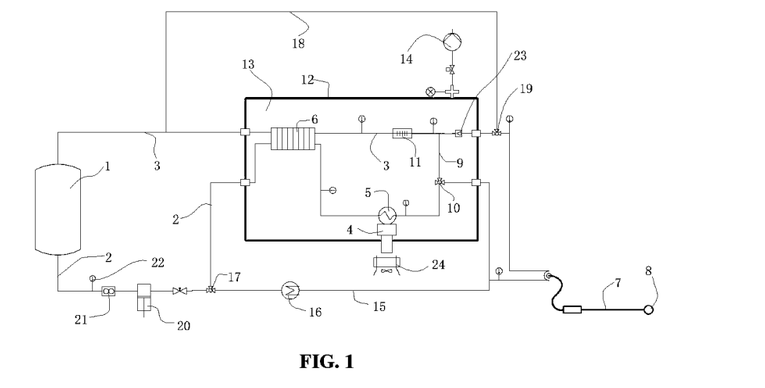
FIG. 1 is a structural schematic diagram of a refrigeration equipment provided in Embodiment 1 of the present application.

The present embodiment comprises a storage tank 1, a delivery pipeline 2, a recovery pipeline 3, a cold energy generator 4, a first cold energy exchanger 5 and a second cold energy exchanger 6. The storage tank 1 stores a cold carrier medium; the delivery pipeline 2 has one end communicated with the storage tank 1 and another end adapted for being communicated with a liquid inlet of a cold energy usage component; the recovery pipeline 3 has one end communicated with the storage tank 1 and another end adapted for being communicated with a liquid outlet of the cold energy usage component; the first cold energy exchanger 5 is mounted on the delivery pipeline 2 and used for cooling the cold carrier medium flowing through the first cold energy exchanger 5 by heat exchange; the cold energy generator 4 provides cold energy to the first cold energy exchanger 5; the second cold energy exchanger 6 has a hot fluid channel mounted on the delivery pipeline 2 and a cold fluid channel mounted on the recovery pipeline 3, wherein, cold energy exchange occurs between the cold fluid channel and the hot fluid channel to precool the cold carrier medium flowing through the hot fluid channel, and the hot fluid channel is connected between the storage tank 1 and the first cold energy exchanger 5.

Figure 3:
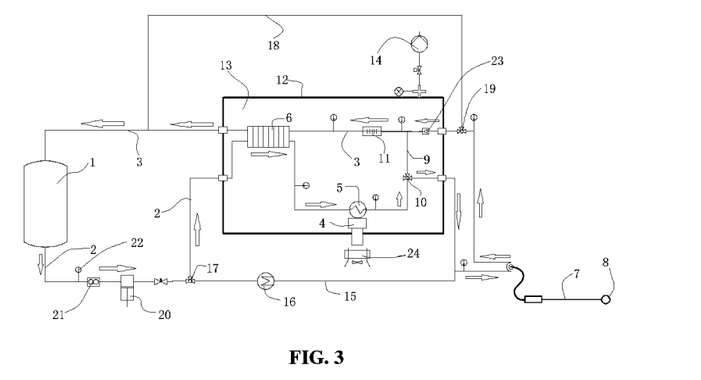
FIG. 3 is a schematic diagram of the flow direction of the cold carrier medium in the refrigerating step for the refrigeration equipment of FIG. 1

When using this refrigeration equipment to carry out cryoablation, the delivery pipeline 2, the recovery pipeline 3 together with the catheter 7 and the cold head 8 of the cold energy usage component are used to circulate the cold carrier medium to flow, and during the flow process, the cold energy generated at the cold energy generator 4 is transferred to the delivery pipeline 2 through the first cold energy exchanger 5, and then transferred into a human body through the catheter 7 for carrying out cryoablation on a target tissue, and after cold energy exchange with the target tissue, the cold carrier medium subsequently flows back to the recovery pipeline 3 through the catheter 7, and at this time, the cold carrier medium still has a residual part of cold energy, then, when the cold carrier medium flows through the recovery pipeline 3, because of the existence of the second cold energy exchanger 6, the residual part of cold energy in the cold carrier medium in the recovery pipeline 3 is transferred to the cold carrier medium in the delivery pipeline 2 via the second cold energy exchanger 6, thereby causing the temperature of the cold carrier medium in the delivery pipeline 2 to drop beforehand.

In the above process, because, on the delivery pipeline 2, the second cold energy exchanger 6 is on an upstream side relative to the first cold energy exchanger 5 where the cold carrier medium in the delivery pipeline 2 has a temperature higher than that of the cold carrier medium in the recovery pipeline 3, it can therefore be ensured that cold energy is transferred from the recovery pipeline 3 to the delivery pipeline 2. By the above process, the residual cold energy of the cold carrier medium in the recovery pipeline 3 can precool the cold carrier medium to reduce the initial temperature of the cold carrier medium entering the first cold energy exchanger 5, therefore, under the condition of the same cold energy exchange amount, such precooled cold carrier medium can reach a lower temperature, so that this way of cryoablation by directly refrigerating liquid at normal pressure is more likely to reach the temperature required for cryoablation, and meanwhile the efficiency of utilization of cold energy is improved.

Specifically, the cold energy generator 4 in the present embodiment is particularly a miniature ultralow-temperature refrigerator that can provide a cold source below −120° C., in the form of a pulse tube, a Stirling engine, a hybrid throttling device, a thermoacoustic device, etc., and there may be one device or multiple devices, and when multiple devices work in combination, they may be combined by being connected in series or in parallel. The cold carrier medium in the present embodiment is a liquid having a solidification point lower than −90° C., for example, medical ethanol.

In order to further reduce the lowest temperature that can be reached by the cold carrier medium, a bypass pipe 9 is further comprised, the bypass pipe 9 is communicated with the delivery pipeline 2 and the recovery pipeline 3 to allow the delivery pipeline 2 and the recovery pipeline 3 to form a precooling looping path connecting the storage tank 1 and the first cold energy exchanger 5 in series; and the bypass pipe 9 is communicated with the delivery pipeline 2 via a first three-way valve 10.

Figure 2:
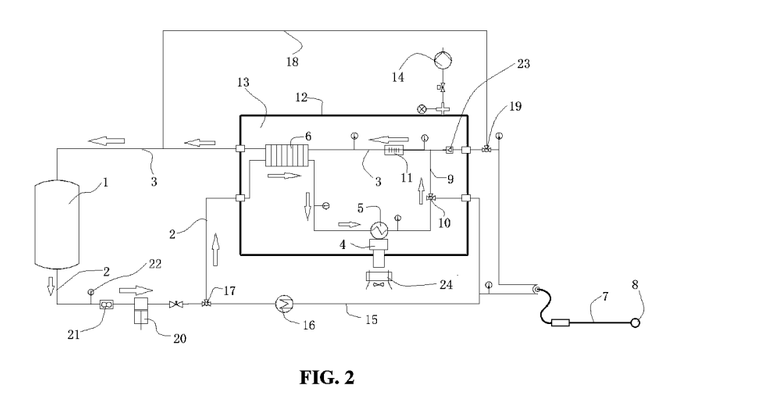
FIG. 2 is a schematic diagram of the flow direction of the cold carrier medium in the precooling step for the refrigeration equipment of FIG. 1.

By using the bypass pipe 9, the cold carrier medium can be precooled before being circulated into the human body for carrying out cryoablation, wherein, in a precooling step, the cold carrier medium comes out from the storage tank 1, sequentially flows through the delivery pipeline 2, the first cold energy exchanger 5, the bypass pipe 9 and the recovery pipeline 3, and finally goes back into the storage tank 1. The precooled cold carrier medium has a reduced temperature to provide a lower initial temperature for entering the cryo-ablating step, and thus the low temperature required for cryoablation can be more easily reached after being cooled again by the first cold energy exchanger 5. Therefore, this measure can further increase the likelihood for the refrigeration equipment to make the cold carrier medium reach the temperature required for cryoablation.

As an improved embodiment of the refrigeration equipment, a cold storage device 11 is further comprised, the cold storage device 11 is mounted on the recovery pipeline 3, communicated with the first cold energy exchanger 5 via the bypass pipe 9, and adapted for storing cold energy coming from the first cold energy exchanger 5. In this embodiment, the cold storage device 11 is specifically a box filled with a cold storage medium having a high specific heat capacity, the recovery pipeline 3 passes through the cold storage device 11 and utilizes a side wall of the pipeline to carry out cold energy exchange with the cold storage medium in the cold storage device 11.

In the precooling step, the cold storage device 11 can store a part of cold energy brought by the cold carrier medium, and after the cryoablation step has started, this part of stored cold energy can precool the cold carrier medium flowing out of the human body, so as to increase the temperature difference between the cold fluid channel and the hot fluid channel at the second cold energy exchanger 6, increase the cold energy exchange rate at the second cold energy exchanger 6, and thus further reduce the temperature of the cold carrier medium in the delivery pipeline 2, and this precooled cold carrier medium can reach a lower temperature after final cooling by the first cold energy exchanger 5. Therefore, this measure can further ensure that the refrigeration equipment can reach the low temperature required for cryoablation, and can further improve the efficiency of utilization of cold energy and reduce waste of cold energy.

In order reduce loss of cold energy, a heat-insulation device 12 is further comprised, the heat-insulation device 12 has a heat-insulation chamber 13 adapted for reducing or eliminating heat conduction to the exterior thereof, with the first cold energy exchanger 5, the second cold energy exchanger 6, the cold storage device 11 and a cold energy output end of the cold energy generator 4 located inside the heat-insulation chamber 13. By using the heat-insulation device 12, loss of cold energy can be prevented during the cold energy exchanging process, and meanwhile the heat preservation effect of the cold storage device 11 is better, as loss of cold energy from the cold storage device 11 is prevented during the cold energy storing process.

Specifically, the heat-insulation device 12 is a box mounted with a vacuumizing device 14 communicated with the heat-insulation chamber 13. The heat-insulation chamber 13 in a near-vacuum state can further reduce the loss rate of cold energy, and thus help the refrigeration equipment further improve the efficiency of utilization of cold energy. The vacuumizing device 14 is a miniature vacuum pump.

As an alternative of the heat-insulation device, the heat-insulation device 12 is a box with the heat-insulation chamber 13 thereof filled with heat insulation substance. Herein, the heat insulation substance may use a heat insulation material such as a polyurethane foamed material or an aerogel.

Figure 4:
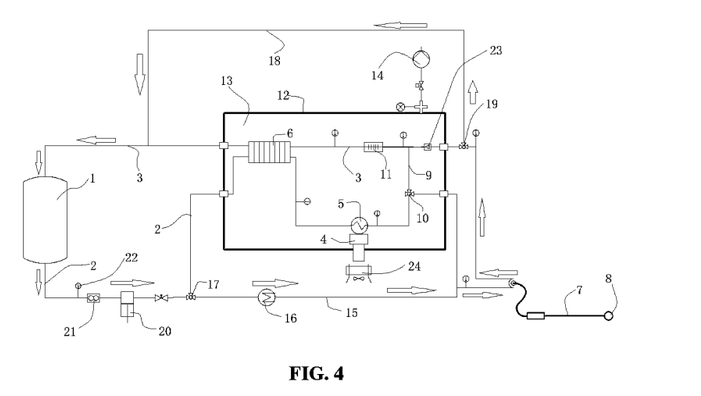
FIG. 4 is a schematic diagram of the flow direction of the cold carrier medium in the rewarming step for the refrigeration equipment of FIG. 1

In order to meet the demands for rewarming the target tissue after refrigerating, the present embodiment also comprises a rewarming looping path for transporting the cold carrier medium in the storage tank to the liquid inlet of the catheter 7 of the cryoablation apparatus after heating the cold carrier medium. In a cryoablation operation, the refrigerated target tissue needs to be rewarmed, and an ideal rewarming process can improve the operative effect of the cryoablation operation and reduce the probability of occurrence of any postoperative complication. The rewarming looping path provided in the present application can heat the cold carrier medium and transport the cold carrier medium to the target tissue through the catheter 7, such a separately arranged rewarming looping path not only can meet the demands of rewarming for the cryoablation operation, but also is very beneficial for accurately controlling the temperature, procedure and time of the rewarming, thereby increasing surgical cure rate and reducing postoperative complications.

Specifically, the rewarming looping path comprises a rewarming pipe 15 with a heating device 16 connected in series, wherein an inlet end of the rewarming pipe 15 is connected by a second three-way valve 17 to an upstream side of an inlet to the hot fluid channel. By connecting the rewarming pipe 15 to the upstream side of the second cold energy exchanger 6 on the delivery pipeline 2, the rewarming pipe 15 is connected in parallel to the first cold energy exchanger 5 and the second cold energy exchanger 6, so that the pipeline for heating the cold carrier medium is independent from the pipeline for cooling the cold carrier medium. Therefore, interference to the heating process of the cold carrier medium caused by residual cold energy of the first cold energy exchanger 5 and the second cold energy exchanger 6 can be prevented in the rewarming step, thereby reducing interference factors in the rewarming process, and making it easier to control the rewarming process.

As an alternative to the above embodiment of rewarming looping path, the rewarming looping path comprises a rewarming pipe 15, wherein an inlet end of the rewarming pipe 15 is connected by a second three-way valve 17 to a side of the delivery pipeline 2 that is located upstream of the first cold energy exchanger 5. In this alternative embodiment, there is no heating device connected in series on the rewarming looping path, and instead, the uncooled cold carrier medium is passed into the catheter for participating in the rewarming process, wherein native heat energy of the human body is utilized to perform rewarming. This measure makes the warming of the target tissue more moderate, thereby reducing any damage caused by the cryoablation operation to healthy tissues.

As a further improvement of the rewarming looping path, the rewarming looping path comprises a rewarming backflow pipeline for connecting the liquid outlet of the catheter 7 of the cryoablation apparatus to a return port of the storage tank 1. The separately arranged rewarming backflow pipeline can make the rewarming process form an independent rewarming loop composed of the storage tank 1, the rewarming pipe 15, the cryoablation apparatus, and the rewarming backflow pipeline, thereby further reducing interference factors in the rewarming process, and making the control of the rewarming process more accurate.

Specifically, the rewarming backflow pipeline comprises a rewarming backflow pipe 18 having both ends thereof communicated with the recovery pipeline 3 and being connected in parallel to the second cold energy exchanger 6, wherein an inlet of the rewarming backflow pipe 18 is connected by a third three-way valve 19 to the delivery pipeline 2. Furthermore, the rewarming backflow pipe 18 is located outside the heat-insulation device 12. As the rewarming backflow pipe 18 is arranged outside the heat-insulation device 12, it can be prevented that the cold energy in the cold storage device 11 or the second cold energy exchanger 6 is brought away by the rewarming backflow pipe 18 when transporting the cold carrier medium after rewarming, so as to improve the utilization rate of cold energy.

In order to ensure smooth circulation of the cold carrier medium, a pumping device 20 is connected in series on the delivery pipeline 2 or the recovery pipeline 3, the pumping device 20 is adapted for providing motive power for the flowing of the cold carrier medium.

Apparently, the afore-mentioned embodiments are merely examples illustrated for clearly describing the present application, rather than limiting the implementation ways thereof. For a person skilled in the art, various changes and modifications in other different forms can be made on the basis of the afore-mentioned description. It is unnecessary and impossible to exhaustively list all the implementation ways herein. However, any obvious changes or modifications derived from the afore-mentioned description are intended to be embraced within the protection scope of the present application.

The invention claimed is:

1. A refrigeration equipment, for supplying cold energy to a cold energy usage component, comprising:
   a storage tank, for storing a cold carrier medium;
   a delivery pipeline, having one end communicated with the storage tank and another end adapted for being communicated with a liquid inlet of the cold energy usage component;
   a recovery pipeline, having one end communicated with the storage tank and another end adapted for being communicated with a liquid outlet of the cold energy usage component;
   a first cold energy exchanger, mounted on the delivery pipeline and used for cooling the cold carrier medium flowing through the first cold energy exchanger by heat exchange;
   a cold energy generator, for providing cold energy to the first cold energy exchanger;
   a second cold energy exchanger, having a hot fluid channel mounted on the delivery pipeline and a cold fluid channel mounted on the recovery pipeline, wherein cold energy exchange occurs between the cold fluid channel and the hot fluid channel to precool the cold carrier medium flowing through the hot fluid channel, and the hot fluid channel is connected between the storage tank and the first cold energy exchanger;
   a bypass pipe communicated with the delivery pipeline and the recovery pipeline to allow the delivery pipeline and the recovery pipeline to form a precooling looping path connecting the storage tank and the first cold energy exchanger in series, wherein the bypass pipe is communicated with the delivery pipeline via a first three-way valve; and
   a heat-insulation device having a heat-insulation chamber adapted for reducing or eliminating heat conduction to the exterior thereof, wherein the first cold energy exchanger, the second cold energy exchanger, the cold storage device, and a cold energy output end of the cold energy generator are located inside the heat-insulation chamber.

2. The refrigeration equipment of claim 1 further comprising a cold storage device mounted on the recovery pipeline, communicated with the first cold energy exchanger via the bypass pipe, and adapted for storing cold energy coming from the first cold energy exchanger.

3. The refrigeration equipment of claim 1 wherein the heat-insulation device is a box mounted with a vacuumizing device communicated with the heat-insulation chamber.

4. The refrigeration equipment of claim 1 wherein the heat-insulation device is a box with the heat-insulation chamber thereof filled with heat insulation substance.

5. The refrigeration equipment of claim 1 further comprising a rewarming looping path for transporting the cold carrier medium in the storage tank to the liquid inlet of the cold energy usage component.

6. The refrigeration equipment of claim 5 wherein the rewarming looping path comprises a rewarming pipe, and wherein an inlet end of the rewarming pipe is connected by a second three-way valve to a side of the delivery pipeline that is located upstream of the first cold energy exchanger.

7. The refrigeration equipment of claim 1 further comprising a rewarming looping path for transporting the cold carrier medium in the storage tank to the liquid inlet of the cold energy usage component after heating the cold carrier medium.

8. The refrigeration equipment of claim 7 wherein the rewarming looping path comprises a rewarming pipe with a heating device connected in series, wherein an inlet end of the rewarming pipe is connected by a second three-way valve to an upstream side of an inlet to the hot fluid channel.

9. The refrigeration equipment of claim 8 wherein the rewarming looping path also comprises a rewarming backflow pipeline for connecting the liquid outlet of the cold energy usage component to a return port of the storage tank.

10. The refrigeration equipment of claim 9 wherein the rewarming backflow pipeline comprises a rewarming backflow pipe having both ends thereof communicated with the recovery pipeline and being connected in parallel to the second cold energy exchanger, wherein an inlet of the rewarming backflow pipe is connected by a third three-way valve to the delivery pipeline.

11. The refrigeration equipment of claim 10 further comprising a heat-insulation device, having a heat-insulation chamber adapted for reducing or eliminating heat conduction to the exterior thereof, wherein the first cold energy exchanger, the second cold energy exchanger, a cold storage device, and a cold energy output end of the cold energy generator are located inside the heat-insulation chamber, and wherein the rewarming backflow pipe is located outside the heat-insulation device.

12. The refrigeration equipment of claim 1 wherein a pumping device is connected in series on the delivery pipeline or the recovery pipeline, and wherein the pumping device is adapted for providing motive power for the flowing of the cold carrier medium.

13. A refrigeration equipment, for supplying cold energy to a cold energy usage component, comprising:
   a storage tank, for storing a cold carrier medium;
   a delivery pipeline, having one end communicated with the storage tank and another end adapted for being communicated with a liquid inlet of the cold energy usage component;
   a recovery pipeline, having one end communicated with the storage tank and another end adapted for being communicated with a liquid outlet of the cold energy usage component;
   a first cold energy exchanger, mounted on the delivery pipeline and used for cooling the cold carrier medium flowing through the first cold energy exchanger by heat exchange;
   a cold energy generator, for providing cold energy to the first cold energy exchanger;
   a second cold energy exchanger, having a hot fluid channel mounted on the delivery pipeline and a cold fluid channel mounted on the recovery pipeline, wherein cold energy exchange occurs between the cold fluid channel and the hot fluid channel to precool the cold carrier medium flowing through the hot fluid channel, and the hot fluid channel is connected between the storage tank and the first cold energy exchanger; and
   a rewarming looping path for transporting the cold carrier medium in the storage tank to the liquid inlet of the cold energy usage component, wherein the rewarming looping path comprises a rewarming pipe, and wherein an inlet end of the rewarming pipe is connected by a second three-way valve to a side of the delivery pipeline that is located upstream of the first cold energy exchanger.

14. A refrigeration equipment, for supplying cold energy to a cold energy usage component, comprising:
   a storage tank, for storing a cold carrier medium;
   a delivery pipeline, having one end communicated with the storage tank and another end adapted for being communicated with a liquid inlet of the cold energy usage component;
   a recovery pipeline, having one end communicated with the storage tank and another end adapted for being communicated with a liquid outlet of the cold energy usage component;
   a first cold energy exchanger, mounted on the delivery pipeline and used for cooling the cold carrier medium flowing through the first cold energy exchanger by heat exchange;
   a cold energy generator, for providing cold energy to the first cold energy exchanger;
   a second cold energy exchanger, having a hot fluid channel mounted on the delivery pipeline and a cold fluid channel mounted on the recovery pipeline, wherein cold energy exchange occurs between the cold fluid channel and the hot fluid channel to precool the cold carrier medium flowing through the hot fluid channel, and the hot fluid channel is connected between the storage tank and the first cold energy exchanger; and
   a rewarming looping path for transporting the cold carrier medium in the storage tank to the liquid inlet of the cold energy usage component after heating the cold carrier medium, wherein the rewarming looping path comprises a rewarming pipe with a heating device connected in series, wherein an inlet end of the rewarming pipe is connected by a second three-way valve to an upstream side of an inlet to the hot fluid channel.

* * * * *